Oct. 14, 1958 F. MEILLAND Plant Pat. 1,761
ROSE PLANT
Filed Feb. 26, 1958
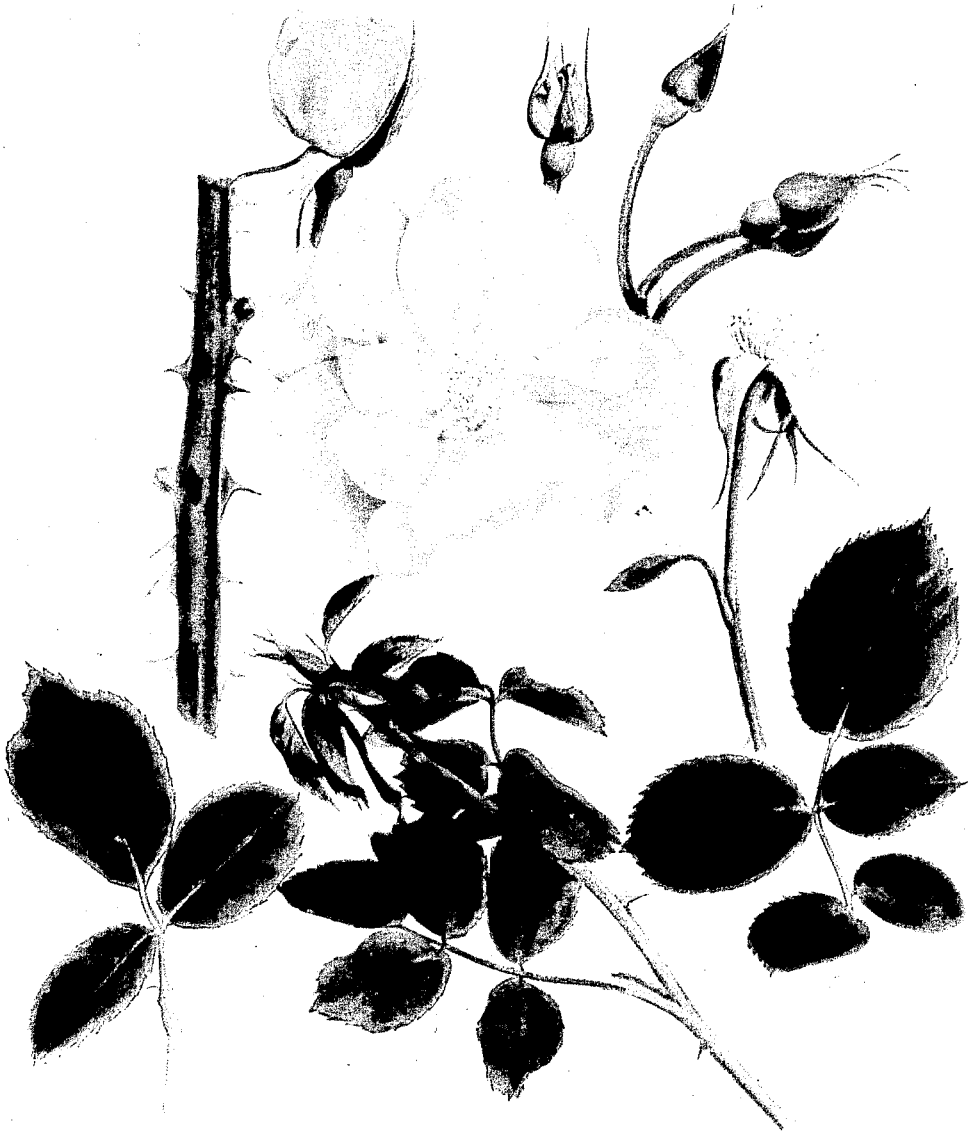
Inventor.
Francis Meilland
By: Robert Robb
Attorneys.

United States Patent Office

Plant Pat. 1,761

Patented Oct. 14, 1958

1,761

ROSE PLANT

Francis Meilland, Cap d'Antibes, Alpes Maritimes, France, assignor to The Conard-Pyle Company, West Grove, Pa., a corporation of Pennsylvania Application February 26, 1958, Serial No. 717,799

Claims priority, application France July 29, 1957

1 Claim. (Cl. 47—61)

The present invention relates to a new and distinct variety of rose plant of the hybrid polyantha class, which was originated by me by crossing an unnamed and unpatented seedling of "Cocorico" (U. S. Plant Patent No. 1,193) × "Moulin Rouge" (U. S. Plant Patent No. 1,298) with the variety "Moulin Rouge."

As the result of this breeding, I have produced a new rose variety which is definitely distinguished from its parents, as well as from all other varieties of which I am aware, and which possesses a unique and desirable combination of characteristics, as evidenced by the following features which are outstanding in the new variety:

(1) A broad and much-branched habit which, combined with the medium height of the plant, makes the variety of particular value for border plantings;

(2) Outstanding floriferousness, with a continuity of color almost without interruption during the entire growing season, but with continuously alternating periods of very heavy and light blooming;

(3) Medium large and beautifully formed blooms of semi-double form, said blooms usually averaging from 10 to 15 petals each; and (4) A remarkably brilliant Iridescent Orient Red general color tonality of the blooms, with an intensity previously unknown in any other rose of this class.

Asexual reproduction of the new variety by budding, as performed in France and at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Hardy; bush; outdoor; seedling; for cut flowers and for garden decoration.

Class: Hybrid polyantha.

Breeding: Seedling.

*Seed parent.*—An unnamed seedling derived from "Cocorico" × "Moulin Rouge."

*Pollen parent.*—"Moulin Rouge."

Propagation: Holds its distinguishing characteristics through succeeding propagations by budding.

*Flower*

Locality where grown and observed: West Grove, Pennsylvania, U. S. A.

Flowers borne: Several to stem; in irregular, flat clusters; on stems of medium length and normal strength.

Quantity of bloom: Abundant, outdoors.

Continuity: Continuous.

Fragrance: Slight. Nature—musk.

Bud:

*Peduncle.*—Short; medium caliper; stiff; rough; with numerous hairs. Color—Lettuce Green, Plate 861, overlaid with Oxblood Red, Plate 00823 where facing sun.

*Before calyx breaks.*—Size—medium. Form—medium; pointed-ovoid; with a conspicuous neck; with foliaceous appendages on the surface of the bud; with slender, foliaceous parts extending beyond the tip of the bud equal to ½ or more of its length.

*As calyx breaks.*—Color—Maroon, Plate 1030.

*As first petal opens.*—Size—medium. Form—medium ovoid. Color: outside—Blood Red, Plate 820; inside—Iridescent Orient Red, Plate 819, grading to Scarlet, Plate 19, over lower quarter of the petal.

*Opening.*—Opens up well.

Bloom:

*Size (when fully open).*—Medium; from 2½ inches to 2¾ inches.

*Petalage.*—Semi-double; from 10 to 15 petals; arranged regularly.

*Form.*—Cupped at first, but becoming open-cupped; petals being at first flat and remaining flat at maturity.

Petals: Leathery; with inside velvety and outside satiny.

*Shape.*—Outer—obovate, with varying number of notches. Inner—obovate; irregular.

This description of a newly opened flower was made from a rose grown outdoors in the month of September, at West Grove, Pennsylvania, U. S. A.:

*Color.*—Outer petal: outside surface—Blood Red, Plate 820/2, with base of petal Spirea Red, Plate 025/3; inside surface—Iridescent Signal Red, Plate 719, grading to Scarlet, Plate 19 at base. Inner petal: outside surface—Blood Red, Plate 820/2, with base of petal washed with Spirea Red, Plate 025/3, and with petal occasionally streaked with Magenta Rose, Plate 027/1; inside surface—Iridescent Signal Red, Plate 719, grading to Scarlet, Plate 19 at base.

This description was made from a rose that was open for 3 days outdoors in the month of September, at West Grove, Pennsylvania, U. S. A.:

*Color.*—Outer petal: outside surface—Geranium Lake, Plate 20/1, with base of petal Spirea Red, Plate 025/3, and with petal often veined with Magenta Rose, Plate 027/1; inside surface—Orient Red, Plate 819, shading to Scarlet, Plate 19, with base of petal Tyrian Rose, Plate 24/2. Inner petal: outside surface—Geranium Lake, Plate 20/1, with base of petal Spirea Red, Plate 025/3, and usually veined with Magenta Rose, Plate 027/1; inside surface—Orient Red, Plate 819, grading to Scarlet, Plate 19, with base of petal Tyrian Rose, Plate 24/3.

*General color effect.*—Newly opened flower—Iridescent Orient Red, Plate 819. 3-days open—Orient Red, Plate 819.

*Behavior.*—Drop off cleanly.

*Flower longevity.*—On bush in garden—3 days in September. Cut roses grown outdoors and kept at living-room temperatures—3 days in September.

*Reproductive organs*

Stamens: Medium number; arranged regularly about pistils.

Filaments: Many; most with anthers; medium length. Color—Naples Yellow, Plate 403 at base, with upper half Spinel Red, Plate 0023.

Anthers: All open at once; from small to medium size; seldom an anther fused with a petaloid. Color—Barium Yellow, Plate 503, edged with Lemon Yellow, Plate 4.

Pollen: From moderate abundance to abundant. Color—yellow.

Pistils: Medium number.

Styles: Uneven; medium length; medium caliper; bunched.

Stigma: Color—light yellow.

Ovaries: All enclosed in receptacle.

Hips: Medium length; globular; with inconspicuous neck; smooth; with walls of medium thickness. Color—red.

Sepals: Permanent; moderately long; spear-shaped.

Seeds: Medium number; medium size.

*Plant*

Foliage:

*Leaves.*—Compound of 5 leaflets; normal abundance; medium size; leathery.

*Leaflets.*—Shape—roundly oval, with apex acuminate. Base—obtuse. Margin—simply serrate.

*Color.*—Mature: upper surface—Spinach Green, Plate 0960; under surface—Spinach Green, Plate 0960/2. Young: upper surface—Parsley Green, Plate 00962/1, lightly overlaid with Maroon, Plate 1030; under surface—Fern Green, Plate 0862, overlaid with Oxblood Red, Plate 00823.

*Rachis (the supporting stem of the compound leaf).*—Medium caliper. Upper side—grooved; hairy. Under side—sparsely prickly.

*Stipules.*—Medium length; medium width; with points of medium length turning out at an angle of more than 45°.

*Disease resistance.*—Comparable to that of the average variety grown under the same cultural conditions at West Grove, Pennsylvania, U. S. A.

Growth:

*Habit.*—Bushy; much-branched.

*Growth.*—From free to vigorous.

*Canes.*—Medium caliper.

*Main stems.*—Bright. Color—Spinach Green, Plate 0960. Prickles—several; color—Fern Green, Plate 0862, overlaid with Brick Red, Plate 016. Hairs—none.

*Branches.*—Bright. Color—slightly darker than Lettuce Green, Plate 861. Prickles—several; color—Oxblood Red, Plate 00823. Hairs—none.

*New shoots.*—Bright. Color—Lettuce Green, Plate 861, overlaid with Oxblood Red, Plate 00823 where exposed to sun. Prickles—several; color—Oxblood Red, Plate 00823. Hairs—none.

I claim:

A new and distinct variety of rose plant of the hybrid polyantha class, substantially as herein shown and described, characterized particularly as to novelty by the unique combination of a broad and much-branched habit, with a medium plant height, outstanding floriferousness, with a continuity of color almost uninterrupted during the entire growing season and accompanied by continuously alternating periods of very heavy and light blooming, an attractive form of semi-double blooms of medium size, and a remarkably brilliant Iridescent Orient Red general color tonality of the blooms of unusual intensity.

No references cited.